United States Patent [19]

Stypulkowski et al.

[11] Patent Number: 4,706,682
[45] Date of Patent: Nov. 17, 1987

[54] EXTERNAL EAR CANAL ELECTRODE TO BE PLACED PROXIMATE THE TYMPANIC MEMBRANE

[75] Inventors: Paul H. Stypulkowski, North Oaks; Christopher van den Honert, Maplewood, both of Minn.

[73] Assignee: Minnesota Mining and Manufacturing Company, St. Paul, Minn.

[21] Appl. No.: 36,209

[22] Filed: Apr. 9, 1987

Related U.S. Application Data

[63] Continuation of Ser. No. 767,324, Aug. 21, 1985, abandoned.

[51] Int. Cl.⁴ .............................................. A61B 5/04
[52] U.S. Cl. .................... 128/642; 128/784; 128/789; 128/802
[58] Field of Search ............... 128/639, 640, 642, 783, 128/784, 785, 788, 789, 800, 802

[56] References Cited

U.S. PATENT DOCUMENTS

| | | |
|---|---|---|
| Re. 28,990 | 10/1976 | Hon et al. |
| 2,047,535 | 7/1936 | Wappler |
| 3,170,046 | 2/1965 | Leale |
| 3,259,128 | 6/1964 | Leight |
| 3,531,992 | 10/1970 | Moore ................................. 73/359 |
| 3,547,104 | 12/1970 | Buffington ......................... 128/604 |
| 3,557,775 | 1/1971 | Mahoney |
| 3,760,812 | 9/1973 | Timm et al. |
| 3,977,411 | 8/1976 | Hughes, Jr. et al. |
| 3,991,755 | 11/1976 | Vernon et al. |
| 4,044,774 | 8/1977 | Corbin et al. |
| 4,050,453 | 10/1977 | Castillo et al. ..................... 128/640 |
| 4,135,518 | 1/1979 | Dutcher .............................. 128/642 |
| 4,146,035 | 3/1979 | Basta |
| 4,150,262 | 4/1979 | Ono |
| 4,161,952 | 7/1979 | Kinney et al. |
| 4,172,451 | 10/1979 | Kline |
| 4,245,645 | 1/1981 | Arseneault et al. |
| 4,280,511 | 7/1981 | O'Neill |
| 4,301,794 | 11/1981 | Tapper ................................. 604/20 |
| 4,325,367 | 4/1982 | Tapper ................................. 604/20 |

(List continued on next page.)

FOREIGN PATENT DOCUMENTS 0084973 3/1983 European Pat. Off. ............ 128/642
105720 5/1974 German Democratic Rep.

OTHER PUBLICATIONS

Axonics, Audit V, A Clinically Programmable Evoked Potential System.
Yanz and Dodds, An Ear-Canal Electrode for the Measurement of the Human Auditory Brain Stem Response, Ear and Hearing, vol. 6, No. 2.
Bochenek et al., Attempts to Rehabilitate Totally Deafened Person By Means of Transdermal Electrostimulation.
Bochenek et al., Electrical Stimulation of the Human Hearing Organ Using Transtympanic Promontory Electrode.
Graham et al., Electrical Stimulation of the Human Cochlea Using Transtympanic Electrode.

Primary Examiner—William E. Kamm
Assistant Examiner—Randy Citrin
Attorney, Agent, or Firm—Donald M. Sell; James A. Smith; William D. Bauer

[57] ABSTRACT

An electrode adapted to be utilized within the external ear canal for applying/recording electrical signals to/-from the neural/neuromuscular system of a person having an external ear canal and adjacent tympanic membrane. The electrode utilizes an elongated flexible body having a proximate end and a distal end. The elongated flexible body is stiff enough to be inserted into the external ear canal but is flexible enough to bend if the electrode is inserted against the tympanic membrane without rupturing the tympanic membrane. A compressible material is mounted at the distal end of the body and an electrically conductive gel is carried by the compressible material. An electrical conductor communicates with the body and electrically couples the conductive gel to the proximate end of the electrode.

19 Claims, 10 Drawing Figures

U.S. PATENT DOCUMENTS

| | | | |
|---|---|---|---|
| 4,333,469 | 6/1982 | Jeffcoat et al. | 128/419 F |
| 4,336,811 | 6/1982 | Beck et al. | 128/784 |
| 4,360,031 | 11/1982 | White. | |
| 4,374,527 | 2/1983 | Iversen. | |
| 4,375,016 | 2/1983 | Harada. | |
| 4,402,330 | 9/1983 | Lindemans. | |
| 4,412,096 | 10/1983 | Edgerton et al.. | |
| 4,414,986 | 11/1983 | Dickhudt. | |
| 4,428,377 | 1/1984 | Zollner et al.. | |
| 4,432,377 | 2/1984 | Dickhudt. | |
| 4,437,475 | 3/1984 | White. | |
| 4,461,304 | 7/1984 | Kuperstein. | |
| 4,539,996 | 9/1985 | Engel | 128/604 |
| 4,592,370 | 6/1986 | Lee et al. | 128/784 |
| 4,601,294 | 7/1986 | Danby et al. | 128/642 |
| 4,622,975 | 11/1986 | Danby et al. | 128/642 |

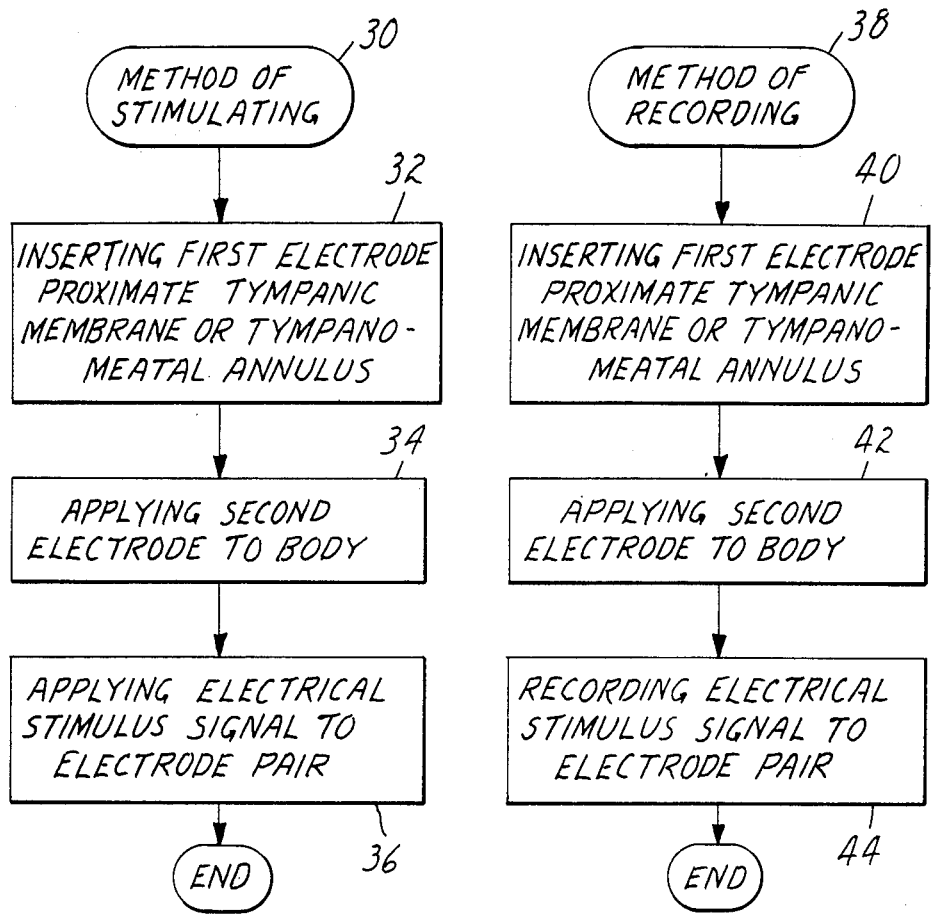

EXTERNAL EAR CANAL ELECTRODE TO BE PLACED PROXIMATE THE TYMPANIC MEMBRANE

This is a continuation of application Ser. No. 06/767,324 filed Aug. 21, 1985, now abandoned.

BACKGROUND OF THE INVENTION

The present invention relates generally to electrodes for applying/recording electrical signals to/from the neural/neuromuscular system of a person. The present invention more particularly relates to such electrodes which are inserted into the external ear canal of a person.

It is well known that electrical stimulation of the auditory system of a person can produce complex perceptions of sounds in human subjects. Experiments by Volta occurred in the early 1800's. Volta inserted metal bars into his external ear canals and passed current between the bars and reported the perception of sound. A series of studies was performed in the late 1930's by Jones, Stevens and Lurie which examined the relationship between various parameters of electrical stimulation and the listed auditory perceps. In these experiments, investigators used metal electrodes placed into saline filled external ear canals to deliver electrical current to the auditory system.

More recently, electrodes surgically implanted into the cochlea, are providing a sensation of hearing in profoundly deaf individuals. The development of cochlear implants has prompted significant additional research in the area of electrical stimulation for hearing augmentation.

Means of stimulating the auditory system which are noninvasive, as opposed to a cochlear implant, are desirable for several reasons. A noninvasive electrode system for auditory stimulation could be used as a functional auditory prosthesis, as a tool in the diagnostic evaluation of potential candidates for cochlear implants or to record the electrical signals generated by an auditory system stimulated by other means.

Several investigators have reported the use of electrodes combined with a saline filled ear canal (known as a Bremmer type electrode) to provide a noninvasive means of auditory stimulation. This approach to the stimulation of the auditory system has a major drawback. Current passed into the saline solution spreads rapidly in all directions through the tissues of the ear and head. The same electrical current which activates the auditory nerve can also stimulate cutaneous nerve fibers thereby producing uncomfortable and, possibly, painful sensations.

Existing systems of auditory stimulation have significant disadvantages. Cochlear implants require surgical invasion of the body. Thus, cochlear implants are not practical for evaluation or diagnostic purposes, which involve temporary stimulation or recording. On the other hand, conventional external ear canal stimulation has significant limitations in dynamic range. The electrical current used in external ear canal stimulation must be above an amount to exceed the hearing threshold but must be below an amount which would produce pain within the external ear canal or, possibly, uncomfortable loud sensations.

SUMMARY OF THE INVENTION

The present invention solves these problems by eliminating surgical invasion while substantially increasing the dynamic range of the stimulation signals which can comfortably be utilized.

The only direct physical pathway from the external ear canal to the inner ear (aside from the skull itself) is the tympanic membrane and the ossicular chain. This tissue connection constitutes the major pathway for current flow between the inner ear and the external ear canal and visa versa. Electrical signals which are generated inside a normally functioning cochlea travel through surrounding tissues and can be recorded from outside of the cochlea. This technique is clinically known as electrocochleography (ECoG). The amplitude of ECoG signals is largest at the surface of the cochlea, the measurement of which is an invasive technique. For noninvasive measurements, the amplitude of ECoG signals is greatest at the tympanic membrane. This supports the hypothesis that the ossicles are the lowest resistance pathway by which current travels between the cochlea and the external ear canal. The present invention provides an electrode and a method of stimulating or recording which takes advantage of this low resistance connection between the inner ear and the external ear canal. The electrodes can be used to either stimulate the inner ear with electrical current or, conversely, to measure the electrical activity originating within the inner ear without an invasive technique.

The present invention provides an electrode adapted to be utilized within the external ear canal for applying-/recording electrical signals to/from the neural/-neuromuscular system of a person having an external ear canal and adjacent tympanic membrane. The electrode has an elongated flexible body having a proximate end and a distal end. A compressible material is mounted at the distal end of the elongate flexible body. An electrically conductive gel is carried by the compressible material and an electrical conductor communicates with the elongate flexible body electrically coupling the electrically conductive gel and adapted to be coupled to a stimulator/recorder at the proximate end. An electrode constructed in this fashion may be placed in the external ear canal with a distal end being proximate the tympanic membrane or tympano-meatal annulus so electrical signals can be applied/recorded to/-from the neural/neuromuscular system.

In an alternative embodiment, the electrically conductive gel is absorbed into the compressible material which, in another alternative embodiment, may also be resilient. The elongated flexible body is stiff enough to enable it to be inserted into the external ear canal but flexible enough to bend if the electrode is pushed against the tympanic membrane without rupturing the tympanic membrane. In another alternative embodiment, an anesthetic may be carried by the compressible material. In other alternative embodiments, a physical fixation device is utilized for physically securing the electrode with respect to the external ear canal. In alternative embodiments, the physical fixation device may be an inflatable cuff, radial fins, a resilient collar or a coiled spring. In an alternative embodiment, adhesive tape adhesively couples the elongated flexible body to the body of the person which in another embodiment may be utilized as a return/reference electrode. In a still further alternative embodiment, the compressible material may be connected to the distal end of the flexible body by a coiled spring.

BRIEF DESCRIPTION OF THE DRAWINGS

The foregoing advantages, construction and operation of the present invention will become more readily apparent from the following description and accompanying drawings in which:

FIG. 2 is a illustration of a method of the present invention;

FIG. 3 is an illustration of an alternative method of the present invention;

DETAILED DESCRIPTION OF THE PREFERRED EMBODIMENTS

Figure 1:
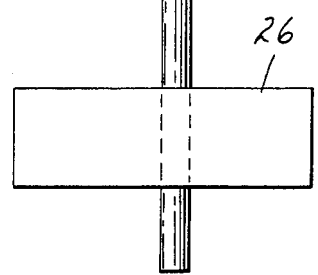
FIG. 1 is an illustration of an electrode of a preferred embodiment of the present invention.

A preferred embodiment of the electrode 10 of the present invention is illustrated in FIG. 1. The electrode 10 is formed from a length of silicone elastomer tubing 12 forming an elongated flexible body. The silicone elastomer tubing 12 is of a sufficient size and sufficient stiffness to allow the insertion of the electrode 10 into the external ear canal but is flexible enough so that the silicone elastomer tubing 12 will bend and not create damage to the tympanic membrane should the electrode 10 be inserted in position proximate to tympanic membrane or tympano-meatal annulus. An example of tubing 12 which is suitable for this purpose is Dow Corning Medical Grade HP Silastic TM tubing with an outside diameter of 0.08 inches (2.03 millimeters) and an inside diameter of 0.077 inches (1.96 millimeters). The tubing 12 has a proximate end 14 suitable to be grasped by the insertion means, such as the health care technician's fingers, and a distal end 16 to be placed into the external ear canal. A compressible material 18 is mounted at the distal end 16 of silicone elastomer tubing 12. In a preferred embodiment, the compressible material is a sponge material such as an open cell compressible foam such as a polyester/polyether sponge and is formed to fit snuggly within the distal end 16 of silicone elastomer tubing 12. In a preferred embodiment, the compressible material 18 has an overall diameter larger than the diameter of silicone elastomer tubing 12. In a preferred embodiment, the dimensions of the compressible material 18 are about 0.25 inch (6.4 millimeters) in diameter and about 0.125 inch (3.2 millimeters) in compressible distance. It is preferred that the compressible material also be resilient. The compressible material 18 cushions the tympanic membrane or tympano-meatal annulus when the electrode 10 is inserted approximately at that position. The resiliency in compressible material 18 will allow the electrode 10 to be withdrawn and reinserted with similar insertion characteristics on subsequent insertions into the external ear canal. A conductive gel is carried by the compressible material at the distal end 16 of silicone elastomer tubing 12. A preferred conductive gel is Red Dot TM No. 2248 Solid Conductive Electrode Gel available from Minnesota Mining and Manufacturing Company. An electrical conductor, namely a wire, 22 is inserted through silicone elastomer tubing 12 from the proximate end 14 to the distal end 16 communicating with the conductive gel 20 carried by compressible material 18. Electrical conductor 22 provides the mechanism for supplying the electrical stimulus signal to the distal end 16 of the electrode 10 or to conduct electrical signals generated by the cochlea from the conductive gel 20 to the proximate end 14 of the electrode 10. It is important to electrically insulate electrical conductor 22 from the walls of the external ear canal and is covered with insulation such as Teflon TM insulation. In the preferred embodiment, electrical conductor 22 is carried in the interior of silicone elastomer tubing 12. In other embodiments, it is envisioned that the electrical conductor could be positioned outside of silicone elastomer tubing 12, spirally wrapped or otherwise communicating with silicone elastomer tubing 12 to create a conductive path between the conductive gel 20 at the distal end 16 and the proximate end 14 of electrode 10. A preferred electrical conductor 22 is a 0.003 inch (0.08 millimeters) diameter wire of 90% platinum and 10% iridium with Teflon TM insultation.

Those features of FIG. 1 heretofor described contain all the essential features of the electrode 10. In addition, the preferred electrode 10 illustrated in FIG. 1 has a second length of silicone elastomer tubing 24 affixed to the proximate end 14 of silicone elastomer tubing 12. One means of securing the second piece of silicone elastomer tubing 24 to silicone elastomer tubing 12 is to make silicone elastomer tubing 24 of a larger diameter and of such a diameter so that a snug fit is developed when silicone elastomeric tubing 24 is placed over or inside of the proximate end 14 of silicone elastomer tubing 12. In a preferred embodiment, electrical conductor 22 may exit the electrode at this point. An alternative electrode 22 could be carried with silicone elastomer tubing 24 the entire length of the electrode or exit somewhere in between. The flexibility characteristics of silicone elastomer tubing 12 are essential for the proper placement of the electrode 10 within the external ear canal. In a preferred embodiment, silicone elastomer tubing 24 is stiffer than and is less flexible than silicone elastomer tubing 12. This silicone elastomer tubing 24 may carry an adhesive tape 26 which can be used to secure the electrode 10 to the external ear, cheek or face of the user providing some mechanical stability to the electrode 10 when it is in place. Any commonly utilized adhesive tape 26 may be utilized such as Micropore TM or Durapore TM tape available from Minnesota Mining and Manufacturing Company.

An electrode constructed as described in FIG. 1 affords several advantages over existing technology. The tip, or distal end 16, of the electrode 10 is composed of a compressible material 18, e.g., a sponge, which is infiltrated with a conductive gel 20. The main body of the electrode 10 is a soft silicone elastomer tubing 12 which allows the insertion of the electrode 10 into the external ear canal. The flexibility of the silicone elastomer tubing 12 combined with the compressible material 18 and conductive gel 20 allows the electrode 10 to be positioned proximate the tympanic membrane or tympano-meatal annulus with little or no discomfort. The contact area of the conductive gel 20 with the tympanic membrane or tympano-meatal annulus results in a low impedance connection for recording or stimulating. It has been found that recording with an electrode of this design results in signals which are significantly greater in magnitude than those obtained with a bare conductive ball electrode and provide a more faithful representation of the electrical signals generated by the cochlea. Recording of inner ear potentials is useful in the clinical diagnosis of ear disorders. Further, electrical stimulation of the inner ear via this electrode 10 could be applied for prosthetic, i.e., hearing augmentation, therapeutic, i.e., tinnitus supression, treatment of hydrops or other inner ear disorders, or diagnostic, i.e., testing of cochlear implant candidates, purposes. The design of the electrode 10 of the present invention affords that current flow into the cochlea is maximized when current is applied directly to the tympanic membrane or tympano-meatal annulus. Less current is lost into the surrounding tissues resulting in (a) lower thresholds for auditory stimulation and (b) less stimulation of cutaneous pain fibers.

Several variations of the electrode 10 could be made without departing from the scope of the present invention. An anesthetic 28 could be incorporated in the compressible material 18. This anesthetic would provide local anesthesia to the stimulus site to further reduce any discomfort from the stimulation or placement of electrode 10 proximate the tympanic membrane or tympano-meatal annulus. A preferred anesthetic to be utilized is lidocaine. Further, it is contemplated that the size of the electrode tip at the distal end 16 could be varied depending upon the optimal use of the electrode, as for example, for stimulation or for recording. For stimulation purposes, a relatively large tip would be optimal since lower current densities at the point of contact would be obtained. A relatively smaller tip at the distal end 16 of the electrode 10 would be optimal for recording purposes where the tip of the electrode 10 would not load or impede the movement of the tympanic membrane.

To insert the electrode 10 into the external ear canal, an insertion tool, typically the health care technician's fingers, grasps the silicone elastomeric tubing 12 and inserts the distal end 16 into the ear canal. The electrode 10 which contains the conductive gel 20, resilient material 18 and, optionally, an anesthetic, if desired, is guided down the external ear canal until the conductive gel 20 of the electrode 10 contacts the tympanic membrane or tympano-meatal annulus. The electrode 10 may then be held in place or may be secured by appropriate physical fixation means, as for example, adhesive tape 26. Electrical conductor 22 may then be connected to the appropriate instrument for either stimulating the inner ear or recording of signals from the inner ear.

FIG. 2 illustrates a method 30 of stimulating the neural/neuromuscular system of a person having a body and an external ear canal and an adjacent tympanic membrane. A first electrode is inserted 32 proximate the tympanic membrane or tympano-meatal annulus. In order to properly localize the current density characteristics and to restrain the electrical current to the appropriate conductive path and to minimize uncomfortableness or pain sensation within the external ear canal, the first electrode should have an elongated flexible body with a proximate end and a distal end. A compressible material is mounted at the distal end of the body. A conductive gel 20 is carried by the compressible material and an electrical conductor communicates with the elongated flexible body and is electrically coupled to the electrically conductive gel. A second electrode is then applied 34 to the body. It is not necessary that the second electrode be of any particular design or that it be applied at any particular location on the body. In general, conventional cutaneous electrodes are applied to the scalp of a person or perhaps to the cheek. The second electrode is a return electrode. An electrical stimulus signal is then applied 36 to the electrode pair consisting of the first electrode inserted in the external ear canal proximate the tympanic membrane or tympano-meatal annulus and the second electrode applied elsewhere to the body.

Similarly, FIG. 3 illustrates a method of recording 38 electrical signals from the neural/neuromuscular system of a person having a body and an external ear canal and adjacent tympanic membrane. A first electrode is inserted 40 into the external ear canal proximate the tympanic membrane or tympano-meatal annulus. A first electrode similar to the electrode described with respect to step 32 of FIG. 2 is appropriate. As in step 34 of FIG. 2, a second electrode is then applied 42 to the body of a person to serve as a reference electrode. Similarily, this electrode needs to be of no special design and maybe a conventional cutaneous electrode applied to the scalp, cheek or other portion of the body. The electrical conductors from the electrode pair consisting of the first electrode and the second electrode are then connected to a recording apparatus and the electrical signals obtained from the inner ear are recorded 44.

Figure 4:
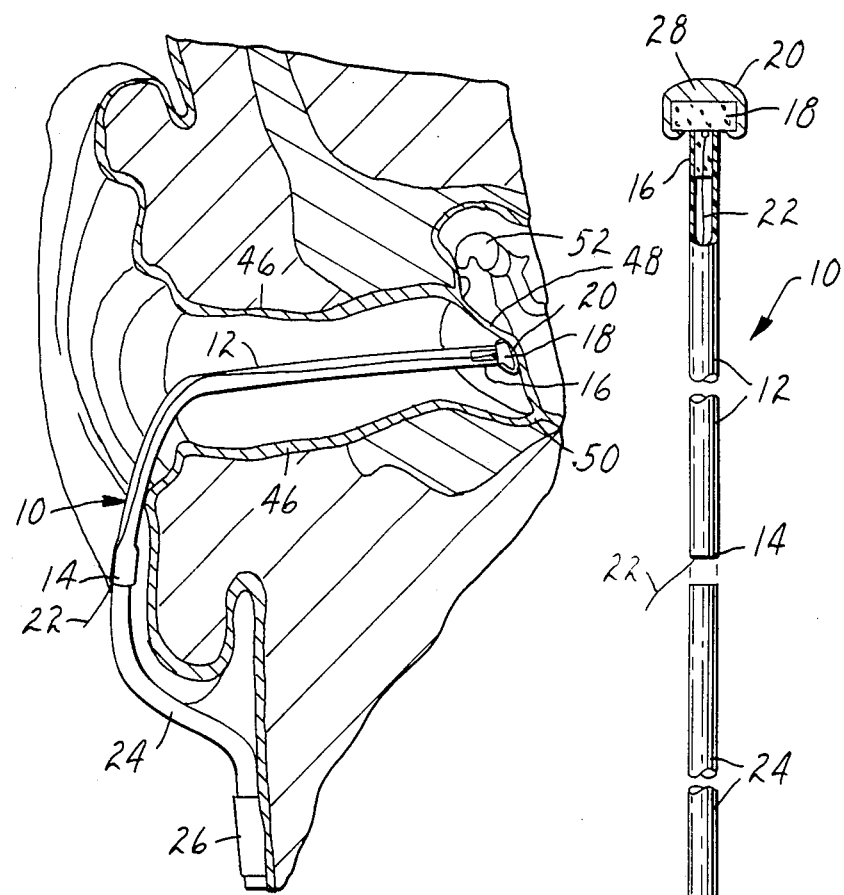
FIG. 4 is an illustration of an electrode of the present invention inserted in an external ear canal.

FIG. 4 shows the electrode 10 of the present invention inserted into the external ear canal 46 of a patient. In particular, the electrode 10 shown in FIG. 1 is illustrated. Silicone elastomer tubing 12 is stiff enough to be guided into the external ear canal but flexible enough to bend once contact is made with the tympanic membrane 48. Alternatively, the electrode 10 could contact the tympano-meatal annulus 50. The conductive gel 20 of the electrode 10 contacts the tympanic membrane 48 or the tympano-meatal annulus 50. Compressible material 18 is compressed by the contact and positioning of the electrode 10 proximate the tympanic membrane 48. Silastic tubing 24 continues outside the external ear canal 46 and is secured to the cheek of the patient by adhesive tape 26. Electrical conductor 22 may then be connected to the appropriate stimulating or recording source or facility.

It can thus be seen, in reference to FIG. 4, that the electrode 10 of the present invention, provides a relatively localized source of stimulation and recording at the tympanic membrane 48 or tympano-meatal annulus 50. Thus, the electrode 10 may take advantage of the most direct current pathway via the ossicular chain 52 to or from the inner ear. The flexibility of the silicone elastomer tubing and the compressibility of the compressible material 18 contribute to the avoidance of pain due to the proximity of the electrode 10 to the tympanic membrane 48 or tympano-meatal annulus 50. Also contributing to the avoidance of pain is the localization of the currents such that stimulations of cutaneous nerve endings in the external ear canal 46 are minimized.

Once the electrode 10 has been placed in the external ear canal 46, it is advantageous to be able to physically fix the electrode 10 with respect to the external ear canal 46. Such fixation will allow consistency of stimulating or recording position as well as prevent damage to the tympanic membrane 48 due to movement of the electrode 10. Several alternative mechanical fixation techniques are described below.

In one alternative embodiment of the electrode 10, the adhesive tape 26 may be made conductive in the form of a cutaneous electrode and the adhesive tape 26 may form the second electrode described in the method of stimulating and the method of recording at steps 34 and 42, respectively, in FIGS. 2 and 3, respectively.

Figure 5:
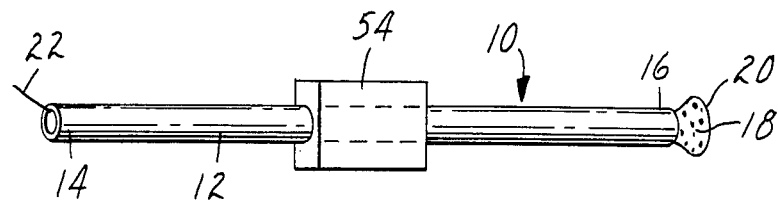
FIG. 5 is an illustration of an alternative embodiment of an electrode of the present invention with an inflatable cuff.

FIG. 5 illustrates an alternative embodiment of an electrode 10. Again, the electrode 10 is formed with an elongated flexible body of a silicone elastomer tubing 12. A compressible material 18 is carried at the distal end 16 of the electrode 10. The compressible material contains a conductive gel 20. An electrical conductor 22 electrically communicates between the end of the electrode 10. Physical fixation of this electrode 10 is achieved through an inflatable cuff 54. Inflatable cuff 54 is preferably a cylindrical balloon constructed from silicone elastomer, preferably 7 mils (0.18 millimeters) thick, fashioned in a manner similar to that of an endotrachial tube and is affixed to silicone elastomer tubing 12. The electrode 10 may be inserted into the external ear canal with the inflatable cuff 54 in a deflated or relatively deflated condition thus allowing insertion of the electrode. Once the electrode has been placed proximate the tympanic membrane or tympano-meatal annulus, the inflatable cuff 54 may be inflated through the insertion of air into its body with a syringe. If removal of the electrode 10 or thereafter desired, the inflatable cuff 54 could be deflated through the reverse process.

Figure 6:
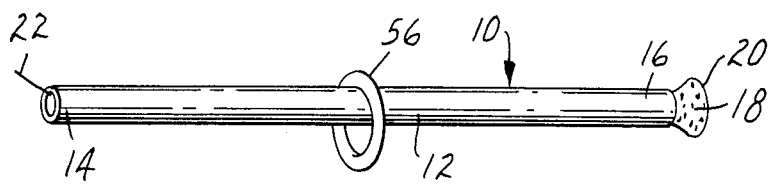
FIG. 6 is an illustration of an alternative embodiment of an electrode of the present invention with an inflatable ring.

FIG. 6 illustrates an electrode 10 similarly constructed as the electrode 10 in FIG. 5. The electrode 10 in FIG. 6 contains as a mechanical fixation means an inflatable ring 56. Inflatable ring 56 may be constructed out of silicone elastomer material. Operating similarly to the inflatable cuff 54 of the electrode 10 of FIG. 5, inflatable ring 56 may be in a relatively deflated condition prior to the insertion of the electrode 10 into the external ear canal. Again, once the electrode 10 is inserted into the external ear canal, inflatable ring 56 may be inflated through conventional inflation techniques such as, for example, the addition to the inflatable ring 56 of air via a syringe. Inflatable ring 56 maybe deflated through the reverse process. One advantage of the inflatable ring 56 over the inflatable cuff 54 is that the external ear canal is not occluded when the electrode 10 is in place. The lack of occlusion of the external ear canal may be advantageous in those situations where the electrode 10 has been utilized for recording purposes. Thus, the tympanic membrane 48 could still receive conventional auditory waveforms through the external ear canal without the external ear canal being obstructed.

Figure 7:
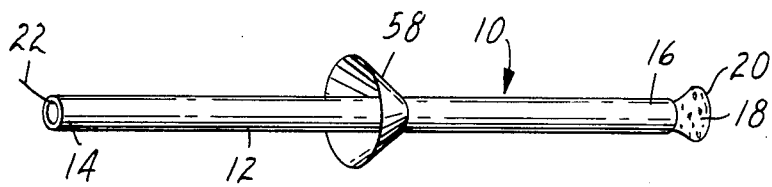
FIG. 7 is an illustration of an alternative embodiment of an electrode of the present invention with a collar.

The electrode 10 illustrated in FIG. 7 contains the silicone elastomeric tubing 12 and compressible material 18 and conductive gel 20 at distal end 16 as well as electrical conductor 22. The electrode 10 of FIG. 7 for mechanical fixation carries a cone-shaped collar 58 affixed to silicone elastomeric tubing 12. The collar 58 may be constructed from a transparent silicone elastomeric material which would afford visability through the external ear canal by the technician while the electrode 10 is being inserted. The narrow end of the cone of the collar 58 is toward the distal end 16 of the electrode 10. Thus, the electrode 10 would be easily inserted into the ear canal and the collar 58 would take the form of the external ear canal and mechanically fix and hold the electrode 10 in place.

Figure 8:
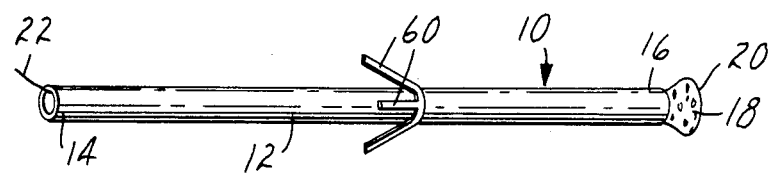
FIG. 8 is an illustration of an alternative embodiment of an electrode of the present invention with fins.

The electrode 10 illustrated in FIG. 8 is similar. Again, silicone elastomeric tubing 12 carries electrical conductor 22 to the distal end 16 where the compressible material and conductive gel are located. For mechanical fixation, the electrode 10 carries stabilizing fins 60 affixed to the silicone elastomeric tubing 12. These fins 60 may be constructed of the same silicone elastomeric material as silicone elastomer tubing 12. The fins are affixed to the silicone elastomer tubing 12 and radiate outward and back away from distal end 16 of electrode 10. Thus, the fins 60 perform a springlike effect when the electrode 10 is inserted into the external ear canal and serve to mechanically hold it in place. Since the fins 60 do not completely transversely surround silicone elastomer tubing 12, the external ear canal is not occluded and the health care technician may visually observe the tympanic membrane while the electrode 10 is being inserted and the external ear canal has left unoccluded following insertion.

Figure 9:
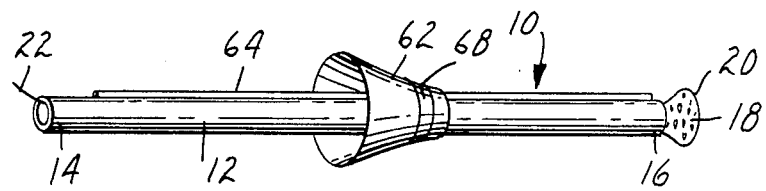
FIG. 9 is an illustration of an alternative embodiment of an electrode of the present invention with a speculum and an anesthetic delivery tube.

The electrode 10 illustrated in FIG. 9 shows the silicone elastomer tubing 12 being utilized in conjunction with a conventional speculum 62. Again, electrical conductor 22 communciates with silicone elastomer tubing 12 to the compressible material and conductive gel 20 at distal end 16 of the electrode 10. Speculum 62 is of conventional speculum design. The speculum is slideably attached to the silicone elastomer tubing 12 at its narrowest opening. The advantages in the use of speculum 62 with the electrode 10 are that conventional ear health care specialists are very familiar with the speculum and could use it as a guide in placing the electrode proximate the tympanic membrane or the tympano-meatal annulus. Again, the interior of the speculum 62 may be utilized by the health care specialist to visualize the external ear canal and tympanic membrane during the insertion of the electrode 10 into the external ear canal 46. An optional feature of the electrode 10 illustrated in FIG. 9 is the use of auxiliary tube 64. Auxiliary tube 64 is coupled longitudinally to silicone elastomer tubing 12 may be utilized either in conjunction with speculum 62 or separately from speculum 62. Through the use of auxialiary tube 64 once the electrode 10 is placed in the external ear canal proximate the tympanic membrane or tympano-meatal annulus an anesthetic may be delivered through the auxiliary tube 64 to the stimulation site of the electrode 10, thus, creating a locally anesthesized area thereby permitting the attainment of higher current densities at that location. It is to be recognized, of course, that auxiliary tube 64 is shown in FIG. 9 for illustrative purposes and auxiliary tubes 64 could take many other forms and shapes within the scope of the present invention. Auxiliary tube 64 could alternatively be located within the interior of silicone elastomeric tubing 12 or could take such other forms as would facilitate the delivery of an anesthetic to the distal end 16 of the electrode once the electrode 10 has been inserted into the external ear canal. In one embodiment speculum 62 has a conductive band 68 on the exterior of the speculum 62 to serve as a return/reference electrode.

Figure 10:
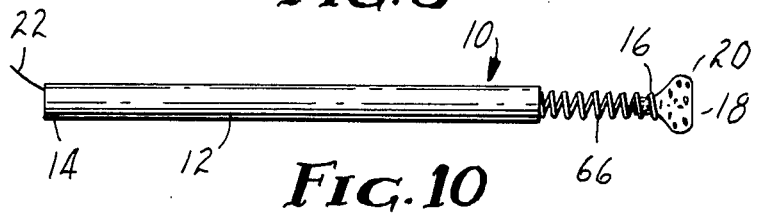
FIG. 10 is an illustration of an alternative embodiment of an electrode of the present invention with a spring tip.

FIG. 10 illustrates an alternative embodiment of the electrode 10 of the present invention. Again, silicone elastomer tubing 12 comprises the elongated flexible body of the electrode 10. Again, electrical conductor 22 communicates with silicone elastomer tubing 12 to a compressible material 18 and an conductive gel 20 at the distal end 16 of the electrode 10. As an additional cushioning means in order to increase the amount of comfort given by the electrode 10 of the present invention a coiled spring 66 is provided between the compressible material 18 and the silicone elastomer tubing 12 at the distal end 16 of the electrode 10. As the compressible material compresses the tympanic membrane 48 coiled spring 66 would contract giving additional flexibility to the electrode 10 and in addition to that flexibility achieved by the compressible material 18 and silicone elastomer tubing 12.

Thus, there has been shown and described a novel external ear canal electrode to be placed proximate the tympanic membrane and methods of stimulating-/recording utilizing an external ear canal electrode placed proximate the tympanic membrane or tympano-meatal annulus. It is to be recognized and understood, however, that various changes and modifications to the design, construction and operation of the present invention may be made by those with ordinary skill in the art without departing from the scope of the following claims.

What is claimed is:

1. An electrode adapted to be utilized within the external ear canal for applying/recording electrical signals to/from the neural/neuromuscular system of a person having an external ear canal and adjacent tympanic membrane comprising:

an elongate flexible body means having a proximate end and a distal end having a distal tip for insertion adjacent the tympanic membrane, being stiff enough to be inserted into the external ear canal and being flexible enough to bend if said electrode is inserted against the tympanic membrane without rupturing the tympanic membrane;

a compressible material mounted at the top of said distal end of said body means;

an electrically conductive gel carried at said distal end of said body means by the distal tip of said compressible material; and an electrical conductor extending along said body means, said electrical conductor being electrically coupled to said electrically conductive gel and adapted to be coupled to a stimulator/recorder at said proximate end of said body means;

whereby said electrode may be placed in the external ear canal with said distal end being proximate the tympanic membrane or tympano-meatal annulus so that neural/neuromuscular system may be electrically stimulated/recorded.

2. An electrode as in claim 1 wherein said compressible material is absorbent and said electrically conductive gel is absorbed into said compressible material.

3. An electrode as in claim 2 wherein said compressible material is also resilient.

4. An electrode as in claim 1 which further comprises an anesthetic being carried by said compressible material.

5. An electrode as in claim 1 which further comprises fixation means for physically securing said electrode with respect to the external ear canal, said fixation means being coupled to said body means.

6. An electrode as in claim 5 wherein said fixation means comprises an inflatable cuff coupled to said elongated flexible body means and adapted to contact the external ear canal.

7. An electrode as in claim 5 wherein said fixation means comprises radial fins coupled to said elongated flexible body means and adapted to contact the external ear canal.

8. An electrode as in claim 5 wherein said fixation means comprises a resilient collar coupled to said elongated flexible body means and adapted to contact the external ear canal.

9. An electrode as in claim 5 wherein said fixation means comprises a speculum having a central opening with a large end a small end, said body means being passed through said opening of said speculum and slideably engaged to said speculum near said small end.

10. An electrode as in claim 9 which further comprises a return/reference electrode affixed to a portion of the exterior surface of said speculum.

11. An electrode as in claim 5 wherein said fixation means comprises an adhesive tape adhesively coupled to said elongated flexible body means and adapted to be secured against the person.

12. An electrode as in claim 11 wherein said adhesive tape utilizes a conductive adhesive and may be utilized as a return/reference electrode.

13. An electrode as in claim 1 wherein said compressible material comprises a sponge.

14. An electrode as in claim 1 wherein said body means comprises silicone elastomeric tubing.

15. An electrode as in claim 1 wherein said compressible material is connected to said distal end of said silicone elastomeric tubing by a coiled spring.

16. An electrode as in claim 15 wherein said coiled spring comprises said electrical conductor.

17. An electrode as in claim 1 wherein said elongated flexible body means is electrically conductive and serves as said electrical conductor.

18. An electrode as in claim 1 wherein said electrical conductor has a resistance of not more than about ten kilohms.

19. An electrode as in claim 1 wherein said body means has a first portion which is more flexble than a second portion of said body means, said first portion of said body means being closer to said distal than said second portion.

* * * * *

UNITED STATES PATENT AND TRADEMARK OFFICE
CERTIFICATE OF CORRECTION

PATENT NO. : 4,706,682
DATED : November 17, 1987
INVENTOR(S) : Paul H. Stypulkowski et al It is certified that error appears in the above-identified patent and that said Letters Patent is hereby corrected as shown below:

Column 2, line 27, "electrodes" should read -- electrode --.

Column 9, line 40, "top" should read -- tip --.

Column 10, line 53, "flexble" should read -- flexible --.

Signed and Sealed this

Tenth Day of May, 1988

Attest:

DONALD J. QUIGG

Attesting Officer

Commissioner of Patents and Trademarks